US00PP34270P2

(12) United States Plant Patent
Hansen

(10) Patent No.: US PP34,270 P2
(45) Date of Patent: May 24, 2022

(54) **X *MANGAVE* PLANT NAMED 'FROSTED JADE'**

(50) Latin Name: ***x Mangave* hybrid**
Varietal Denomination: Frosted Jade

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,994

(22) Filed: Jan. 10, 2022

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Karen M Redden

(57) ABSTRACT

A new and unique x *Mangave* plant named 'Frosted Jade' characterized by moderate to slow growth rate; short, compact, rounded habit and lanceolate foliage with glaucous blue-green margins and light minty-green centers above and below, with small, sharp, firm mucro and small semi-flexible marginal teeth.

2 Drawing Sheets

Botanical classification: x *Mangave* hybrid.
Variety denomination: 'Frosted Jade'.

STATEMENT REGARDING PRIOR DISCLOSURES UNDER 37 CFR 1.77(B)(6)

No plants of x *Mangave* 'Frosted Jade' have been sold, in this country or anywhere in the world, nor has any disclosure of the new plant been made prior the filing date of this application.

BACKGROUND OF THE INVENTION

The present invention relates to the new and distinct x *Mangave* plant, 'Frosted Jade' that was discovered by the inventor at a wholesale perennial nursery in Zeeland, Mich., USA as a whole plant mutation of x *Mangave* 'Frosted Elegance' U.S. Plant Pat. No. 32,289. The new plant was discovered on Jan. 23, 2021. Through trials at the same nursery the plant was referred to by the code 21-SP-MANG-1002. The new plant has been successfully asexually propagated by removal of plantlets after coring at the same nursery in Zeeland, Mich. The asexual propagation by basal offsets has been found to produce stable and identical plants that maintain all the unique characteristics of the original plant.

BRIEF SUMMARY OF THE INVENTION

X *Mangave* 'Frosted Jade' differs from its parent as well as all other *Manfreda, Agave* and x *Mangave* known to the applicant. The parent has a wider blue-green margin and narrower more chartreuse center and lacks the light, minty-green center variegation.

The most similar known X *Mangave* cultivar known to the inventor are: *Agave* 'Galactic Traveler' (not patented), *Agave* 'Joe Hoek' (not patented); x *Mangave* 'Arctic Fox' (not patented), 'Bloodlines' (not patented), 'Dragon Lady' U.S. Plant Pat. No. 33,985, 'Pineapple Upsidedown Cake' (not patented), 'Queen for a Day' U.S. Plant Pat. No. 32,711, 'Racing Stripes' U.S. Plant Pat. No. 31,251, 'Shadow Waltz' U.S. Plant Pat. No. 31,601 and 'Sweet Tooth' U.S. Plant patent application Ser. No. 17/300,984.

'Galactic Traveler' has a much larger habit, very miniscule marginal spines and the variegation is more silver in the center and the margin is yellow. 'Joe Hoek' has a larger habit, very miniscule marginal spines, and the center variegation is more medium green surrounded by a yellow edge between the dark green margin and center. 'Arctic Fox' has a larger plant habit with longer, more arching foliage, with a longer more acute apex, the leaf surfaces are less glaucous and more evident dark grey-purple spotting. 'Bloodlines' has narrower, thicker foliage, a more purplish margin, and the marginal teeth are larger and more burnt orange-colored. 'Dragon Lady' has a larger more arching habit, the foliage is more folded, more sinuate and less glaucous, and the center variegation is more yellowish with more intense reddish-purple spotting throughout. 'Pineapple Upsidedown Cake' has a larger and broader habit, narrower leaves that are yellowish with reddish spotting in the center with a deep green margin and small flexible marginal teeth. 'Queen for a Day' has a larger habit, longer and broader leaves that are variegated with a olive-green in the center and dark purplish-green on the margins with larger marginal teeth. 'Racing Stripes' has a larger habit with a faster grow rate and foliage that is narrower, more lustrous and less glaucous and the center variegation is more chartreuse. 'Shadow Waltz' has longer narrow arching leaves with broad dark green margin and light green to chartreuse center and the marginal teeth are larger. 'Sweet Tooth' has a striated grey and celadon center variegation with larger burnt orange teeth that are curved backward.

The new plant, 'Frosted Jade', is unique from all these variegated *Agave*, x *Mangave* and *Manfreda* known to the inventor by the following combined traits:

1. Short, compact, rounded mound habit;
2. Foliage lanceolate with small semi-flexible marginal teeth and small, firm, sharp, apical mucro;
3. Foliage has narrow glaucous blue-green margins and light minty-green center above and below;
4. Moderate to slow growth rate.

BRIEF DESCRIPTION OF THE DRAWINGS

The photograph of the new plant demonstrates the overall appearance of the new plant including the unique traits as a one-year-old plant grown in a container initially in a greenhouse in Zeeland, Mich. with water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
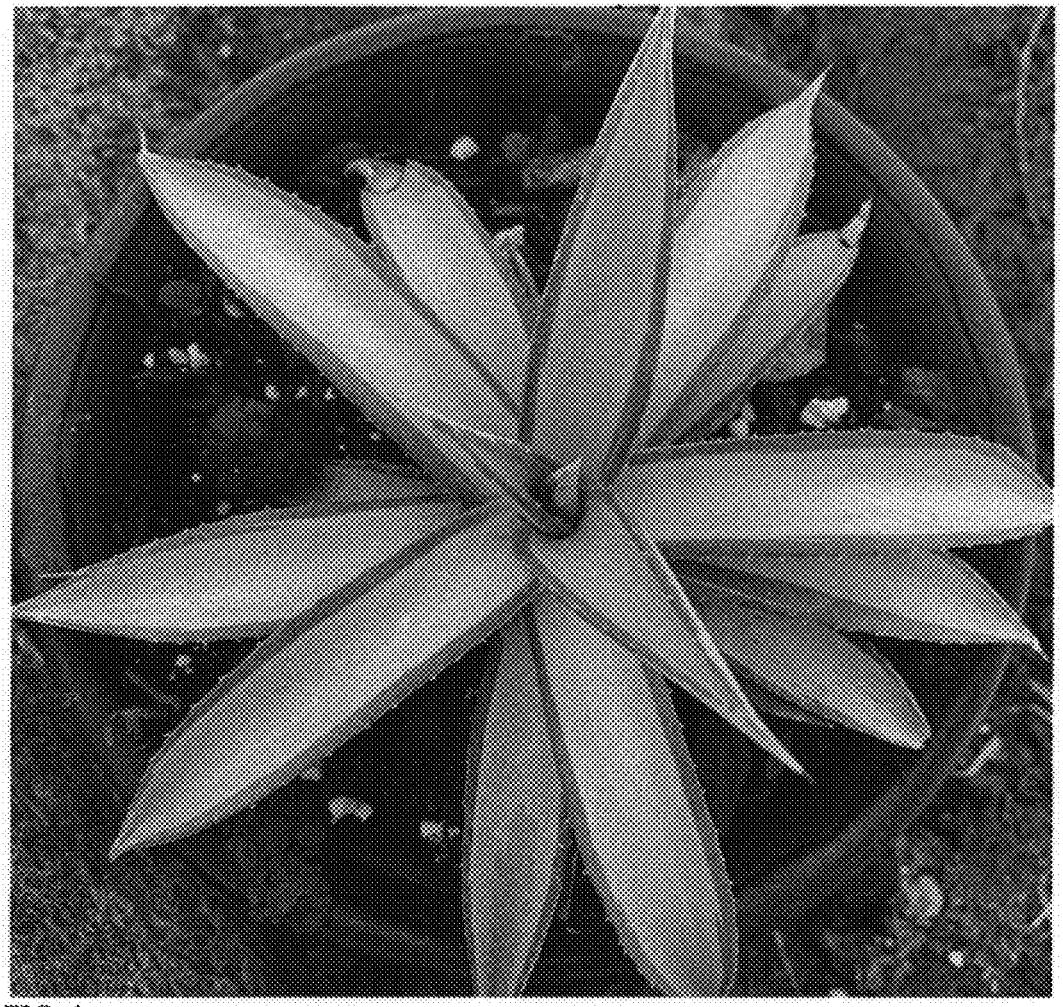
FIG. 1 shows the new plant from above.
Figure 2:
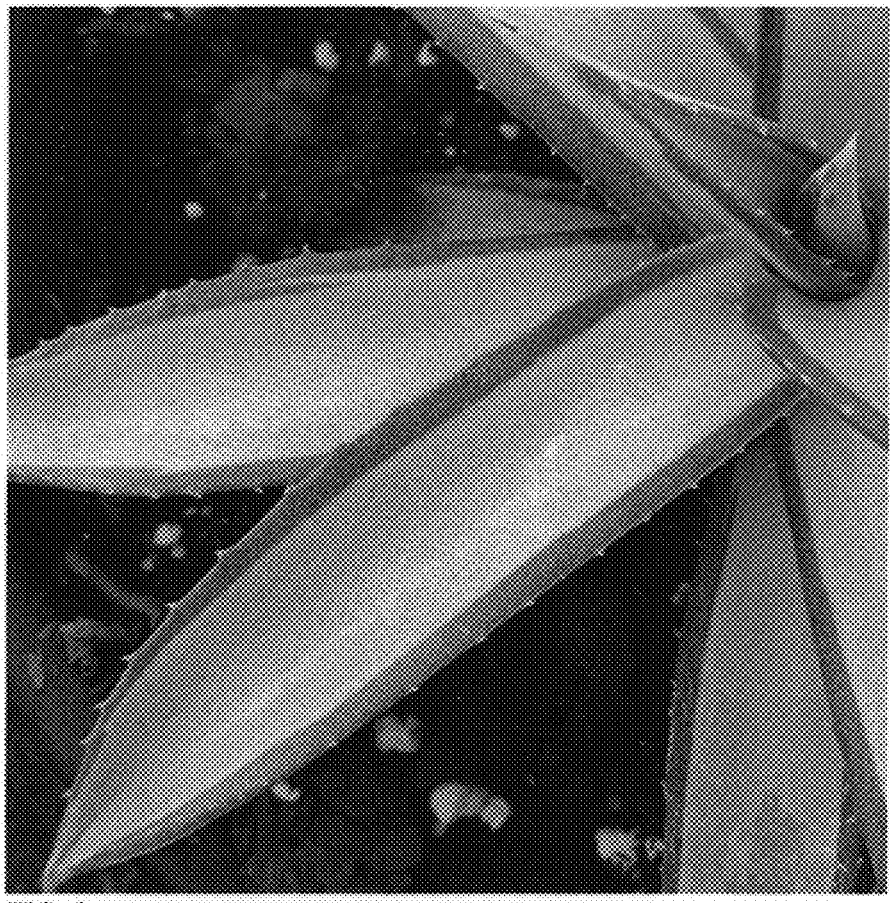
FIG. 2 shows a close-up of the foliage of the new plant.

The following descriptions and color references are based on the 2015 edition of The Royal Horticultural Society Colour Chart except where common dictionary terms are used. The new plant, x *Mangave* 'Frosted Jade', has not been observed under all possible environments. The phenotype may vary slightly with different environmental conditions, such as temperature, light, fertility, moisture and maturity levels, but without any change in the genotype. The following observations and size descriptions are of a one-year-old plant in a commercial wholesale greenhouse in Zeeland, Mich. with supplemental water and fertilizer as needed.

Botanical classification: *Agave* times x *Mangave* hybrid;

Variety denomination: 'Frosted Jade';

Parentage: A whole plant mutation of x *Mangave* 'Frosted Elegance';

Propagation: Removal offsets after coring;

Time to initiate roots: About 28 days;

Growth rate: Moderate;

Crop time: About 24 to 30 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 23 leaves radially emerging and outwardly reaching from central rhizome, producing a symmetrical rounded mound;

Plant size: Foliage height about 6.5 cm tall from soil line to the top of the leaves and to about 17 cm wide at the widest point at soil line;

Foliage description: Lanceolate; simple; sarcous; fibrous; glabrous; margins finely dentate with semi-flexible teeth; apex acute with short firm mucro; base truncate, sessile, semi-clasping;

Leaf size: To about 10.5 cm long, about 20 mm wide near middle and 5 mm thick near base, average about 8 cm long, 16 mm wide and 4 mm thick; typically bi-laterally symmetrical; glabrous and glaucous above and below; adaxial margin to about 4 mm wide and center to about 12 mm wide, abaxial margin about 2.5 mm wide and center to about 15 mm wide; teeth to about 0.8 mm long and 0.8 mm across at base about 3.7 mm apart; mucro about 2 mm long and 0.5 mm wide;

Foliage fragrance: None observed;

Leaf blade color:

*Adaxial.*—Young margin between RHS N138A and RHS N138B, center nearest RHS 194D.

*Abaxial.*—Young margin between RHS N138A and RHS N138B, center between RHS 194C and RHS 191D.

*Adaxial.*—Mature margin between RHS 191C and RHS N138A, center between RHS 193B and RHS 193C.

*Abaxial.*—Mature margin between RHS 146B and RHS N138C, center nearest blend between RHS 138D and RHS 193B.

*Teeth.*—Abaxial and adaxial on young foliage between RHS 193B and RHS 157D, on mature foliage nearest RHS 191D.

Mucro: Terminal spine; firm; straight; sharply pointed; about 2 mm long and 0.5 mm wide;

*Mucro color.*—Adaxial and abaxial on young foliage between RHS 165A and RHS 166B; on mature foliage nearest RHS 200A.

Petiole: Sessile;

Veins: Parallel; not distinct;

Flowering and fruiting have not yet been observed.

Disease resistance: X *Mangave* 'Frosted Jade' has not been observed to be resistant or susceptible to diseases common to other x *Mangave* beyond that which is normal for x *Mangave, Agave* or *Manfreda.*

Growing conditions: The new plant is xeromorphic and survives well with minimal water once established.

Winter hardiness: at least from USDA zone 9 to 11; full extent of winter hardiness has not been tested.

I claim:

1. A new and distinct cultivar of ornamental x *Mangave* plant named 'Frosted Jade' as herein described and illustrated.

* * * * *